United States Patent [19]

Chow

[11] Patent Number: 5,382,258
[45] Date of Patent: Jan. 17, 1995

[54] ARTHROSCOPIC KNOT TYING DEVICE

[75] Inventor: James C. Y. Chow, Mount Vernon, Ill.

[73] Assignee: Linvatec, Fla.

[21] Appl. No.: 114,437

[22] Filed: Aug. 30, 1993

Related U.S. Application Data

[63] Continuation of Ser. No. 947,827, Sep. 21, 1992, Pat. No. 5,318,579.

[51] Int. Cl.⁶ .............................................. A61B 17/00
[52] U.S. Cl. .................................. 606/148; 606/205; 606/207; 289/17
[58] Field of Search ............... 606/139, 144, 148, 205, 606/207, 208, 103; 289/17

[56] References Cited

U.S. PATENT DOCUMENTS

| | | | |
|---|---|---|---|
| 671,337 | 4/1901 | Gibson | 606/148 |
| 3,763,860 | 10/1973 | Clarke | 128/830 |
| 3,834,395 | 9/1974 | Santos | 606/139 |
| 5,084,058 | 1/1992 | Li | 606/139 |
| 5,100,421 | 3/1992 | Christoudias | 606/147 |
| 5,176,691 | 1/1993 | Pierce | 606/144 |
| 5,257,637 | 11/1993 | El Gazayerli | 606/139 |

FOREIGN PATENT DOCUMENTS

| | | | |
|---|---|---|---|
| 453256 | 1/1929 | Germany | 606/148 |
| 185025 | 3/1956 | Germany | 606/139 |
| 1091700 | 10/1960 | Germany | 606/207 |
| 2210574 | 6/1989 | United Kingdom | 606/207 |
| 167006 | 12/1964 | U.S.S.R. | 606/144 |
| 649416 | 2/1979 | U.S.S.R. | 606/139 |
| WO92/12674 | 8/1992 | WIPO | 606/139 |

Primary Examiner—Stephen C. Pellegrino
Assistant Examiner—Jeffrey A. Schmidt
Attorney, Agent, or Firm—Polster, Lieder, Woodruff & Lucchesi

[57] ABSTRACT

A method for closing an incision (I) deep within a patient's body (B) with a suture (S). A medical instrument (C) has arms 1 and 2 for openings and closing opposed jaws (3,4). Each jaw has a pair of openings (3A-3B, 4A-4B). A knot (K) is formed using the ends (S1, S2) of the suture. For this purpose, the ends of the suture are withdrawn from the body. This allows the surgeon to form a proper surgical knot. After forming the knot, the suture ends are inserted through the respective Fairs of openings. The surgeon can now draw the knot tightly down on the incision to close it by inserting the jaws end of the instrument into the patient's body while applying a slight pulling force on the ends of the suture. The surgical knot thus made will not thereafter loosen.

6 Claims, 2 Drawing Sheets

ARTHROSCOPIC KNOT TYING DEVICE

This is a continuation of copending application Ser. No. 07/947,827, filed on Sep. 21, 1992, now U.S. Pat. No. 5,318,579.

BACKGROUND OF THE INVENTION

This invention relates to arthroscopic and/or endoscopic surgery and more particularly, to a method of performing a surgical procedure and a surgical appliance useful in performing the method.

In performing surgical procedures, one problem commonly encountered is tying off stitches closing an incision in such a way as to prevent the knot from loosening or coming undone. If the surgery is performed in a locale where the patient's skin is, or can be drawn back, exposing the surgical site, tying off stitches so they do not come undone should not be a problem. In arthroscopic and/or endoscopic surgeries where the surgical site is deep inside the body so the site is not readily accessible, this is not easily done. Because the surgical site is usually also very small, the surgeon is typically working in a very confined area and is probably using an endoscope in order to view the work he is performing. As a consequence, he does not have the space to make the type of surgical knot he would like to make, or to make it sufficiently tight it will not later loosen. The knot he uses in this situation is usually a slip knot, or some variation thereof, rather than a double knot which is preferred for closing incisions. If a knot becomes undone in this latter instance, the surgical site must be reopened so the stitches can be tied off again. This is not acceptable. It would be preferable if the surgeon could prepare the knot ex situ where there is adequate room for him to work, but current surgical procedures and instruments do not allow him to do so.

SUMMARY OF THE INVENTION

Among the several objects of the present invention may be noted to provision of a surgical method of performing a surgical procedure especially an arthroscopic and/or endoscopic surgical procedure; the provision of such a method in which a length of suture used in closing an opening can be drawn from the surgical site to a location where the surgeon has ample space to tie a surgical knot; the provision of such a method which thereafter permits the surgeon to readily return the knotted portion of the suture back to the site and tighten it in place so it does not thereafter slip or loosen; the provision of such a method which allows the surgeon to securely and permanently tie off a suture so it does not thereafter have to be retied; the provision of a pair of forceps for use by the surgeon is performing the method, the forceps having a pair of jaws through which the suture can be inserted; the provision of such forceps which allows the surgeon to draw the suture away from the surgical site (i.e., external to the body) where the surgeon has ample room to prepare a preferred surgical knot and then transfer the knot back to the site using forceps; and, the provision of such a surgical appliance which is easy to use and can also be used as a conventional surgical instrument.

The method of the invention, briefly stated, comprises using a surgical instrument such as forceps at a surgical site, especially an arthroscopic and/or endoscopic surgical site which is not readily accessible. A suture for closing an opening at the site is to be knotted with a surgical knot. The ends of the suture are withdrawn from the body and a knot is formed using the free ends of the suture. After the knot is formed, the ends of the suture adjacent the knot are drawn into respective openings in the instrument. The knotted end of the suture is then transferred back to the surgical site using the instrument so a firm knot is tied at the surgical site which will not subsequently loosen. Other objects and features will be in part apparent and in part pointed out hereinafter.

BRIEF DESCRIPTION OF THE DRAWINGS

Corresponding reference characters represent corresponding parts throughout the drawings.

DESCRIPTION OF THE PREFERRED EMBODIMENT

Figure 1:
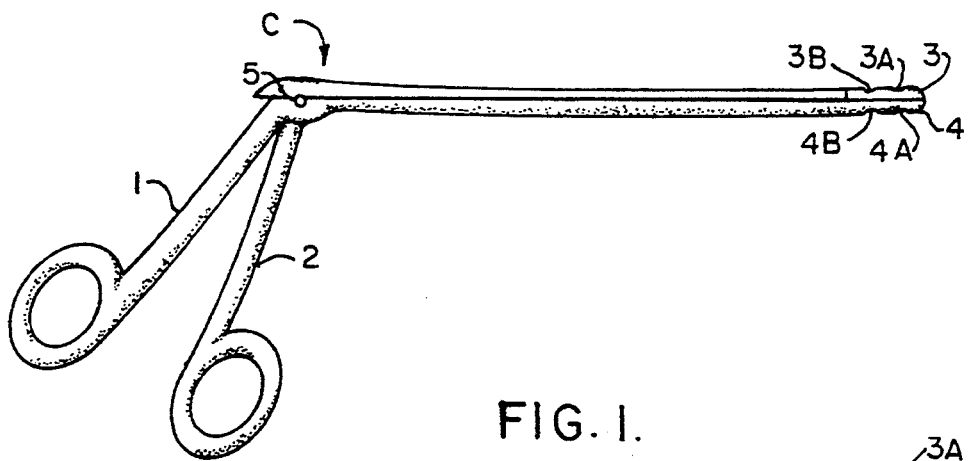
FIGS. 1–2 illustrates a surgical instrument of the present invention.

Referring to the drawings, a surgical site X is located within a patient's body B. During performance of surgery, for example, an arthroscopic surgery at site X, an incision I is made. A suture S is subsequently used by the surgeon to close the incision. Heretofore, if site X was remote within the patient's body, the surgeon's ability to tie a satisfactory knot K in the suture has been severely limited. The type of knot preferred for tying off the suture is a double knot which does not loosen over time. Because of the inaccessibility of site X, the surgeon has previously only been able to use a slip knot or similar knot which may loosen over time. If this happens, there is a good chance the incision will not properly close and additional surgery may be required.

In accordance with the present invention, a surgical instrument C (see FIGS. 1 and 2) has a pair of cooperating arms 1 and 2 with respective jaws 3 and 4 at the end of the arms. Instrument C is an elongate, thin instrument for being readily positioned at a remote site inside the patient's body. The jaws are located at the inner end of the instrument. The arms are hingedly connected at 5, this hinge point being at the opposite, external end of the instrument. Because of the limited accessibility of site X, a cannula L is inserted in an opening O1 in the patient's skin N and the inner end of the cannula is positioned adjacent the site. To help the surgeon see what he is doing, an endoscopic device D is inserted through a second opening O2 in the skin and also positioned adjacent the surgical site.

Figure 3:
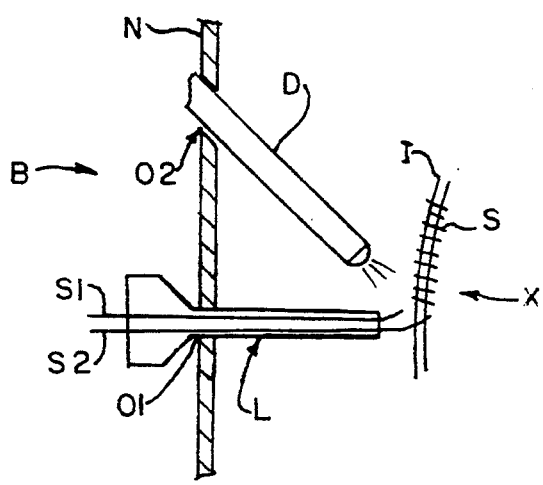
FIGS. 3–7 illustrate the method of the present invention by which a surgeon can tie a proper surgical knot in a suture using the instrument.
Figure 4:
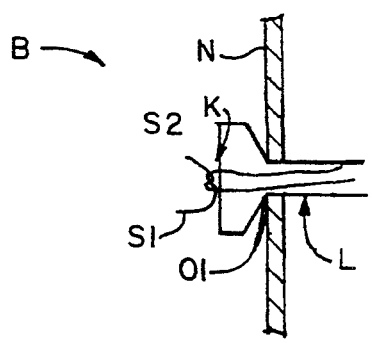

As shown in FIG. 3, once the surgeon has sewn up the incision using suture S, he draws the ends S1 and S2 of the suture out of the patient's body through the cannula. Next, the surgeon ties an appropriate knot K with the ends of the suture (see FIG. 4).

Figure 2:
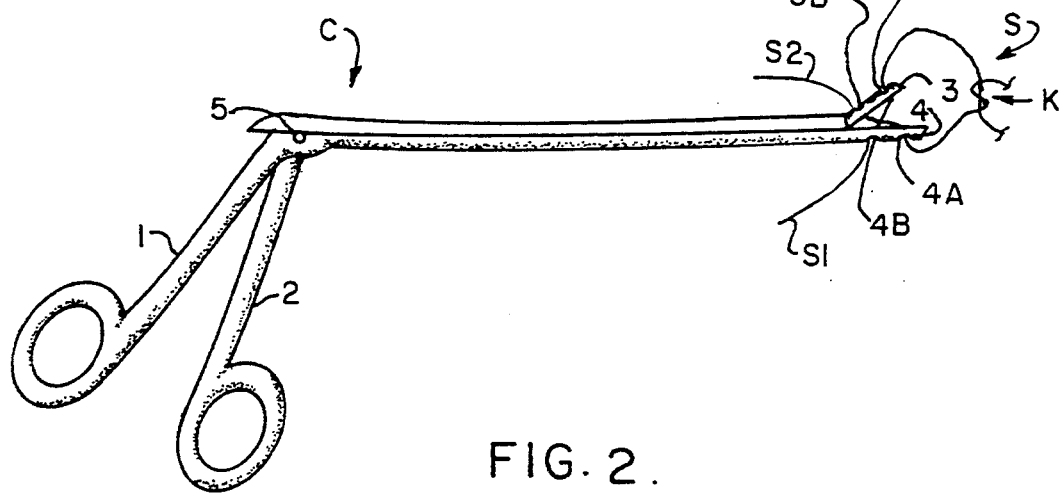
Figure 5:
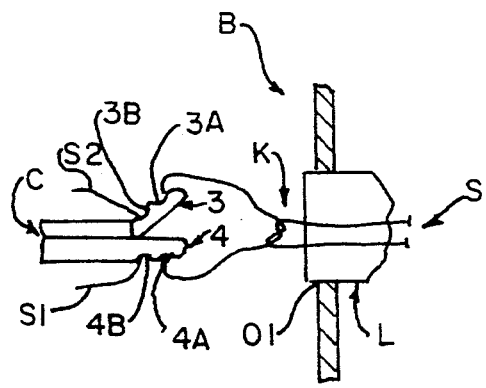
Figure 6:
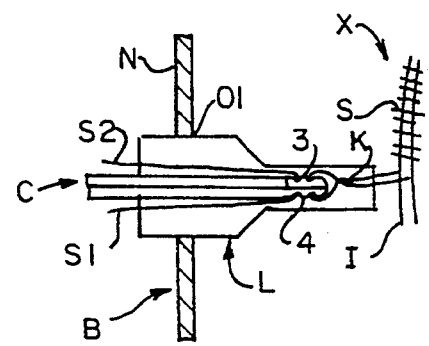
Figure 7:
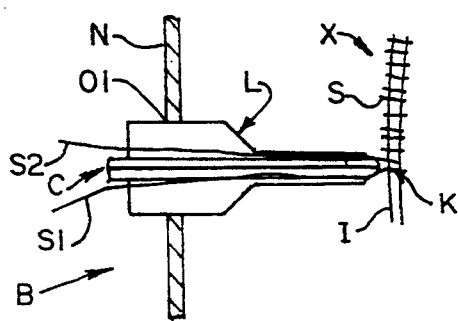

By manipulating arms 1 and 2 of instrument, the surgeon can open the jaws of the instrument, as seen in FIGS. 2 and 5. Each jaw has a pair of openings. Jaw 3 has openings 3A and 3B, and jaw 4 has openings 4A and 4B. Once the surgeon has prepared knot K, he routes each end of the suture into one of the openings of each respective pair, and out the other opening. Thus, as shown in the drawings, suture end S1 is inserted into opening 4A from the outside of the jaw 4 into the jaw, and then draws the end back out of the jaw through opening 4B. The same thing is done with end S2. Once the suture ends are inserted through the instrument jaws, the jaws are closed, and the suture ends are drawn back along the shank of the instrument. The elongate, shank portion of instrument C is sized to fit through cannula L as shown in FIGS. 6 and 7. To draw knot K down onto the incision, the surgeon exerts a constant pulling force on suture ends S1 and S2. As he does so, he inserts the jaws end of the instrument C through cannula L. The movement of the instrument toward the incision site and the pressure on the ends of the suture effectively moves knot K until it is tightly drawn up against the incision, closing it.

To tie a double knot, the surgeon releases the pressure on the ends of the suture and then withdraws the instrument back out of the cannula. The ends of the suture remain threaded through the openings in jaws 3 and 4, but because there is no force on them, knot K does not move. Once withdrawn from the patient's body B, the surgeon re-opens jaws 3 and 4 and pulls the ends of the sutures out of the jaws. He then repeats the above steps, tying a new knot K with the ends of the suture, reinserting the suture ends through the openings in the jaws, closing the jaws, and reinserting the jaw end of the instrument into the cannula to draw this second knot down onto the first. After the knot is completed, instrument I is withdrawn as before. The ends S1, S2 of the suture can then be cut.

Figure 8:
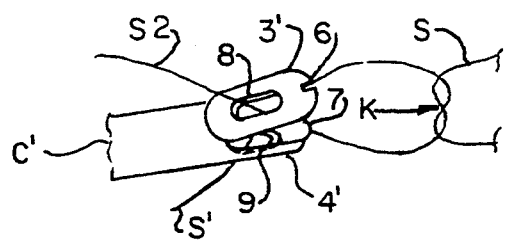
FIGS. 8–10 illustrate alternate embodiments of the surgical instrument useful in performing the method.
Figure 9:
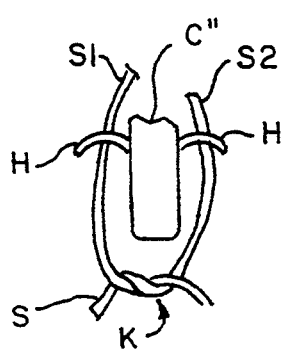
Figure 10:
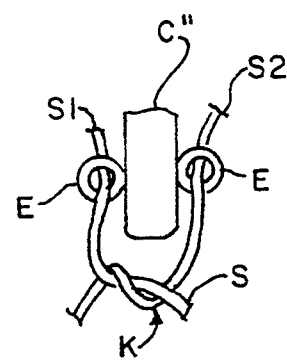

Referring to FIGS. 8–10, an alternate embodiment C' of the instrument is shown in FIG. 8, and is similar to the instrument C previously described. Now, however, jaws 3' and 4' each have a notch, 6 and 7 respectively at their outer, tip end. Now, instead of two holes in each jaw, there is only one, 8 and 9 respectively. As seen, once knot K is formed, end S1 is routed through notch 6 in jaw 3' and opening 9 in jaw 4'. End S2 is routed through notch 7 in jaw 4' and opening 8 in jaw 3'. Once this is done, the jaws are closed and the instrument is operated as before. Alternately, and as shown in FIGS. 2 and 10, hooks H or eyelets E can be formed on opposite sides of an instrument C''. The free ends S1 and S2 of the suture are captured by, or pass through the hooks or eyelets. It will be understood that the size of instrument C'', regardless of whether it has hooks or eyelets, must be such as to pass through cannula L so the knot can be drawn down on the incision.

In view of the foregoing, it will be seen that the several objects of the invention are achieved and other advantageous results are obtained.

As various changes could be made in the above constructions without departing from the scope of the invention, it is intended that all matter contained in the above description or shown in the accompanying drawings shall be interpreted as illustrative and not in a limiting sense.

Having thus described the invention, what is claimed and desired to be secured by Letters Patent is:

1. A medical instrument for use by a surgeon performing an endoscopic or arthroscopic procedure in which an incision is made at a remote site within the patient's body, the instrument being usable by the surgeon to tie a surgical knot with with a suture at the surgical site to close the incision, comprising:
    an elongate instrument body;
    a pair of jaws located at one end of the instrument body, one of the jaws being movable with respect to the other to open and close the jaws;
    handle means at the other end of the instrument body graspable by the surgeon for holding the instrument and for manipulating the jaws;
    hinge means positioned at the end of the instrument body adjacent the handle means, the handle means and the jaws being operably connected to the hinge means for manipulation of the handle means by the surgeon to operate the hinge means to open and close the jaws; and,
    means for inserting one end of the suture through one of the jaws, and the other end of the suture through the other jaw, the inserting means comprising a pair of separate, spaced channels formed in a jaw body of each jaw intermediate respective sides of the jaw, at least one of said channels being for the respective end of the suture to be threaded into the jaw through one of the openings therein and out of the jaw through the other channels therein, inserting the ends of the suture through the respective jaws allowing the surgeon to form a surgical knot in the suture with the ends of the suture remote from the surgical site, insert the ends of the suture through the jaws after the knot is formed, draw the knot down on the surgical site by inserting the elongate instrument body, jaws end first, through a cannula, and tightening the knot, after the knot is drawn down on the incision, by opening the jaws to exert opposite pulling forces on the respective ends of the suture.

2. The medical instrument of claim 1 wherein both of the channels in each of the jaws are intermediate the length of the respective jaws in an in-line relationship.

3. The medical instrument of claim 1 wherein one channel in each jaw comprises a notch formed in the outer end of the jaw and the other opening comprises an channel formed intermediate the length of the jaw.

4. Knot tying apparatus for use by a surgeon to close an incision made in a patient's body with a suture, the surgeon using a cannula to access the surgical site, the apparatus comprising:
    an elongate instrument body sized to fit through the cannula;
    a pair of jaws formed at the end of the body that is sized to be inserted through the cannula, one of the jaws being fixed and the other jaw being movable relative to said fixed jaw to open and close said jaws;
    handle means at the opposite end of said body graspable by the surgeon for holding the apparatus and opening and closing said jaws, said handle means being hingedly connected to said jaws for movement of said handle means by the surgeon to open and close said jaws; and,
    means formed in each jaw for inserting the ends of the suture through said jaws after a knot is formed by the surgeon with the ends of the suture, said suture inserting means comprising first and second separate spaced channels formed in each jaw at least one of said channel being intermediate respective sides of the jaw and through which the suture ends are threaded, the surgeon opening said jaws to thread the suture ends through channels, then closing said jaws and inserting said elongate body through the cannula to draw the knot down on the incision, and then re-opening said jaws to tighten the knot.

5. The apparatus of claim 4 wherein the channels in each jaw are formed intermediate the length of said jaw.

6. The apparatus of claim 4 wherein a first channel in each jaw comprises a notch formed at the outer end of said jaw, and the second channel is formed in said jaw intermediate the length thereof.

* * * * *